United States Patent [19]

Finnieston et al.

[11] Patent Number: 4,765,319
[45] Date of Patent: Aug. 23, 1988

[54] HAND SPLINT

[76] Inventors: Alan Finnieston, 2480 W. 82nd St., Hialeah, Fla. 33016; William E. Burkhalter, 8905 SW. 97 Ave., Miami, Fla. 33176; Franklin Reyes, 10450 SW. 84 Ave., Miami, Fla. 33156

[21] Appl. No.: 934,856

[22] Filed: Nov. 25, 1986

[51] Int. Cl.⁴ ............................................. A61F 5/04
[52] U.S. Cl. .................................. 128/87 R; 128/77; 128/89 R
[58] Field of Search .................. 128/87 R, 89 R, 90, 128/91 R, 77; 2/16, 161 R, 161 A, 159, 20, 162, 163

[56] References Cited

U.S. PATENT DOCUMENTS

| 315,512 | 4/1885 | Kearns | 128/89 R |
|---|---|---|---|
| 2,070,810 | 2/1937 | Saling | 128/89 R |
| 2,206,404 | 7/1940 | Jones | 128/89 R |
| 3,769,970 | 11/1973 | Swanson | 128/87 A X |
| 3,819,796 | 6/1974 | Webster et al. | 128/90 |
| 3,924,272 | 12/1975 | Allen et al. | 2/16 |
| 3,942,522 | 3/1976 | Kinnier et al. | 128/89 R X |
| 4,062,073 | 12/1977 | Rhee | 2/16 |
| 4,382,439 | 5/1983 | Shen | 128/89 R X |
| 4,483,333 | 11/1984 | Wartman | 128/90 |

FOREIGN PATENT DOCUMENTS 3006362  8/1981  Fed. Rep. of Germany .... 128/87 R

Primary Examiner—Richard J. Johnson
Assistant Examiner—Charles H. Sam
Attorney, Agent, or Firm—Larson and Taylor

[57] ABSTRACT

A multi-function hand splint for immobilizing a hand, wrist, and distal forearm of a user includes a sleeve made of a semi-rigid material. The sleeve includes an elongate shell of substantially C-shape with the opening of the C-shape located along the M-L plane of the forearm. This shell includes a dorsal shell portion and a volar shell portion. Extending from the dorsal shell portion is a dorsal hood having a metacarpal hood portion and a phalanx hood portion. The metacarpal hood portion forms a dorsiflexion angle of between 60° to 80° with the axis of the forearm so that a comfortable maximal dorsiflexion of the wrist is achieved. The metacarpal hood portion also forms a hood angle of between 75° to 90° with the phalanx hood portion. A palm arch supports extends from the volar shell portion in order to maintain the hand in the dorsal hood with the wrist in dorsiflexion and the metacarpal-phalangeal joints at an angle greater than about 90° to 105°. A thumb opening is provided between the dorsal hood and palm arch support so that the thumb of the user extends therethrough and all joints of the thumb are free to move. Suitable straps are preferably used to hold the sleeve in radial abutment with the hand, wrist, and distal forearm of the user.

9 Claims, 2 Drawing Sheets

HAND SPLINT

FIELD OF THE INVENTION

The present invention relates generally to devices for immobilizing a hand and wrist of a user, and more particularly to a unitary, universal hand splint which allows use of the fingers and thumb while the hand and wrist are immobilized.

Background of the Invention

Various universal hand splints have been used in the art to stabilize a wrist of a user in a neutral or slight dorsiflexion. Such hand splints are easily applied and removed. However, one of the major problems with hand and wrist injuries is a development of metacarpal-phalangeal joint extension deformities. These various prior art hand splints have not satisfactorily eliminated this problem.

A unitary device for immobilizing the thumb, hand, and wrist of a user is disclosed in U.S. Pat. No. 4,382,439 (Shen). The disclosed device includes a shell formed of an integral piece of semi-rigid material having portions shaped to receive the upper forearm, hand, and thumb. This shell is substantially C-shaped with a longitudinal opening along the upper or dorsal side of the device. The wrist dorsiflexion angle is disclosed as being between 10° and 40°, and preferably 30°. A thumb opening is provided on the side of the device through which the top of the thumb extends while the fingers extend almost fully out of the device.

The use of opposed dorsal and palm arch splints to immobilize a forearm, wrist, and hand therebetween has been disclosed in prior art. For example, in U.S. Pat. No. 568,951 (Kearns), the opposed splints are designed to achieve a wrist dorsiflexion angle of 80° to 75° and a radial deviation angle of approximately 18°. A similar device is disclosed in U.S. Pat. No. 315,512 (Kearn) in which the dorsiflexion angle is much smaller. It should be noted that the splints in the both of these patents result in the immobilization of the fingers of the user, although the thumb is evidently not immobilized.

In U.S. Pat. No. 1,469,315 (Hansard), a wrist support device including opposed splints is disclosed in which the splints terminate before the metacarpal-phalangeal joints. This allows full movement of the fingers of the user and additionally allows a sidewards movement of the wrist so that the device can be used as a wrist support for such sports as golf or billiards in which a back and forth movement of the wrist is a defective action.

SUMMARY OF THE INVENTION

In accordance with the present invention, a unitary hand splint for mobilizing the hand, wrist, and distal forearm of a user is provided. The hand splint includes a sleeve in which the hand, wrist, and distal forearm of the user are received. This sleeve is made of a semi-rigid material. The sleeve includes an elongate shell extending over the wrist and distal forearm which has a substantially C-shape in lateral cross section with the opening of the C-shape located along the M-L plane (side) of the forearm. This shell includes a dorsal shell portion and a volar shell portion. Extending from the dorsal shell portion is a dorsal hood including a metacarpal hood portion which covers the dorsum of the hand and a phalanx hood portion which covers the proximal phalanges. The phalanx hood portion terminates at the proximal phalanges. The metacarpal hood portion forms a dorsiflexion angle between 60° to 80° with the axis of the forearm so that a comfortable maximal dorsiflexion of the wrist is initially achieved. The metacarpal hood portion forms a hood angle of between 75° to 90° with the phalanx hood portion. A palm arch support extends from the volar shell portion. This palm arch support extends adjacent the matacarpal hood portion in order to maintain the hand in the dorsal hood with the wrist in dorsiflexion by abutment with the metacarpal hood portion and the metacarpal-phalangeal joints at an angle of greater than about 90° to 105° by abutment of the proximal phalanges with the phalanx hood portion. A thumb opening is also provided between the dorsal hood and palm arch support so that the thumb of the user extends therethrough and all joints of the thumb are free to move. The hand splint also includes a holding means which holds the sleeve in radial abutment with the hand, wrist and distal forearm of the user.

In a preferred embodiment of the hand splint of the present invention, the hood angle is slightly less than 90° and the dorsiflexion angle is about 75°. In addition, the line formed by the apexes of the hood angle forms an angle of about 60° with respect to the longitudinal axis of the hand projected on the metacarpal hood portion. Further, the line formed by the apexes of the hood angle when projected onto the M-L plane forms an angle of about 80° with the forearm axis.

In the preferred embodiment, the holding means includes at least two straps and associated securing means for securing the straps in tension across the opening of the C-shaped shell in order to radially compress the distal forearm portion. This holding means further includes a strap and associated securing means for securing this latter strap in tension between the palm arch support and the dorsal hood to maintain the hand in the dorsal hood. Preferably, the sleeve is covered on an inside portion thereof with a resilient material and a plurality of apertures are provided through the sleeve and resilient material. The opening of the C-shaped shell is preferably on the little finger side of the hand.

It is an advantage of the present invention that the development of metacarpal-phalangeal joint extension deformities is avoided by the placing of the metacarpal-phalangeal joints into flexion.

It is also an advantage of the present invention that even though the hand, wrist, and distal forearm of the user are prevented from movement, the user still retains full thumb motion and full PIP flexion and extension.

It is a further advantage of the present invention that the dorsal hood aids in the correction of dorsal edema of the hand and fingers which is a usual accompaniment of most hand and wrist injuries.

Another advantage of the present invention is that the hand splint maintains gentle contact over the dorsum of the hand and thus positions the hand in the dorsal hood. Therefore, the hand splint of the present invention is additionally usable to treat metacarpal fractures and certain fractures of the proximal phalanx.

Still another advantage of the present invention is that the tightening of the sleeve with the straps to provide some soft tissue compression allows adjustment for the size of the forearm to accommodate for changes in the forearm circumference due to subsistence of edema and muscle atrophy with time.

Other features and advantages of the present invention are stated in or apparent from a detailed description of a presently preferred embodiment of the invention found hereinbelow.

DETAILED DESCRIPTION OF THE PREFERRED EMBODIMENT

Figure 1:
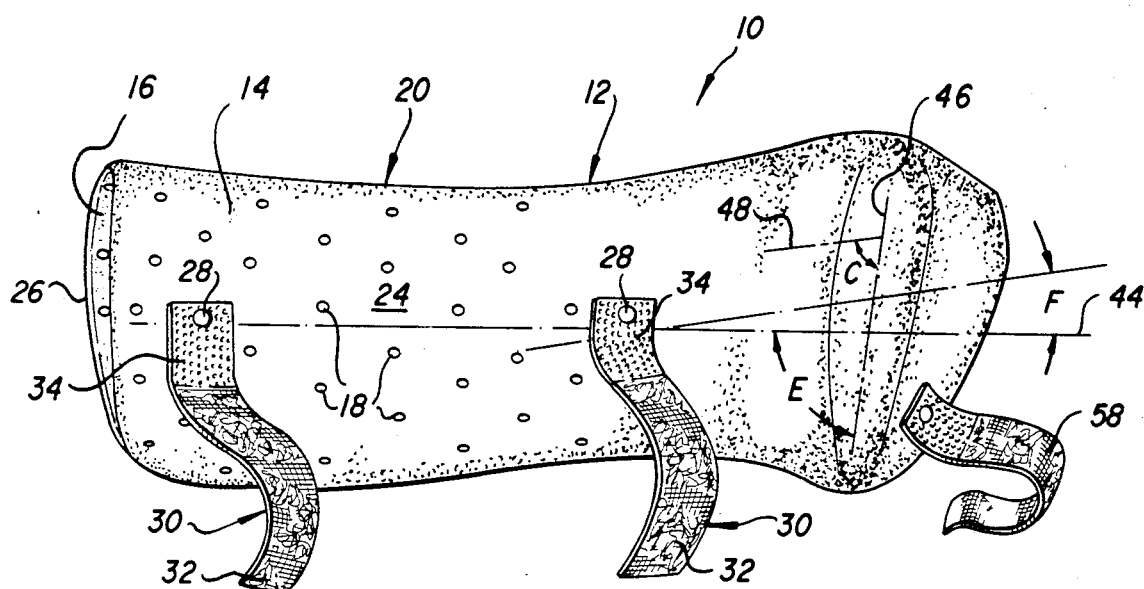
FIG. 1 is dorsal (posterior) view of the hand splint of the present invention.

With reference now to the drawings in which like numerals represent like elements throughout the several views, a hand splint 10 according to the present invention is depicted. It should be appreciated that the anatomic position of the forearm which is the basis for the nonmenclature describing the principle planes of the forearm is based upon a person standing in an upright position with the hands and arms extended and hanging downwards with the palms of the hands facing forward. Thus, the posterior or dorsum of the hand is the back of the hand, while the anterior or volar of the hand is the palm of the hand. In this position, the lateral side of the hand (away from the center of the body) is the thumb side whereas the medial side of the hand (closer to the body) is the small finger side. It should also be appreciated that hand splint 10 is depicted as a hand splint for the right hand of a user, and that a hand splint for a left hand would simply be a mirror image of hand splint 10.

Hand splint 10 includes a one piece sleeve 12 in which the hand, wrist, and distal forearm of the user are received. Sleeve 12 is made of an outer material 14 of molded polyethylene which is lined with an inner material 16 of polyethylene foam. Perforations 18 are provided in outer material 14 and inner material 16 to allow air circulation to the skin of the user.

Sleeve 12 includes an elongate shell 20 which extends over the wrist and distal forearm of the user. Shell 20 is substantially C-shaped in lateral cross section. Longitudinal opening 22 of the C-shape of shell 20 is located in the M-L plane of the forearm, and preferably along the little finger side of hand splint 10 as depicted.

Shell 20 includes a dorsal shell portion 24 and a volar shell portion 26. Attached to dorsal shell portion 24 by use of rivets 28 are two velcro straps 30. Velcro straps 30 include a fibrous portion 32 which are suitably attached to respective hook portions 34. Located on volar shell portion 26 longitudinally opposite velcro straps 30 are rings 36 which are similarly attached by rivet. It should be appreciated that velcro straps 30 are fed through rings 36 and back upon themselves in order for fibrous portions 32 to attach to hook portion 34 and to hold volar shell portion 26 and dorsal shell portion 24 together.

Sleeve 12 also includes a dorsal hood 38 which extends from dorsal shell portion 24. Dorsal hood 38 is formed by a metacarpal hood portion 40 and a phalanx hood portion 42. Metacarpal hood portion 40 forms a dorsiflexion angle A with the forearm axis 44 of between 60° to 80°. Dorsal hood 38 also includes a hood angle of between 75° to 90° formed by metacarpal hood portion 40 and phalanx hood portion 42. In the preferred embodiment of hand splint 10, dorsiflexion angle A is preferably about 75° (+/−50) and hood angle B is preferably slightly less than 90°.

Figure 3:
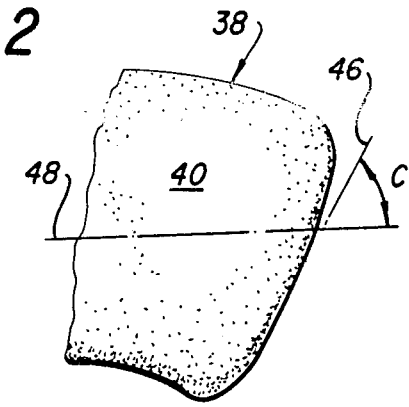
FIG. 3 is a partial view toward the back of the hand splint viewed along the line 3—3 of FIG. 2.
Figure 6:
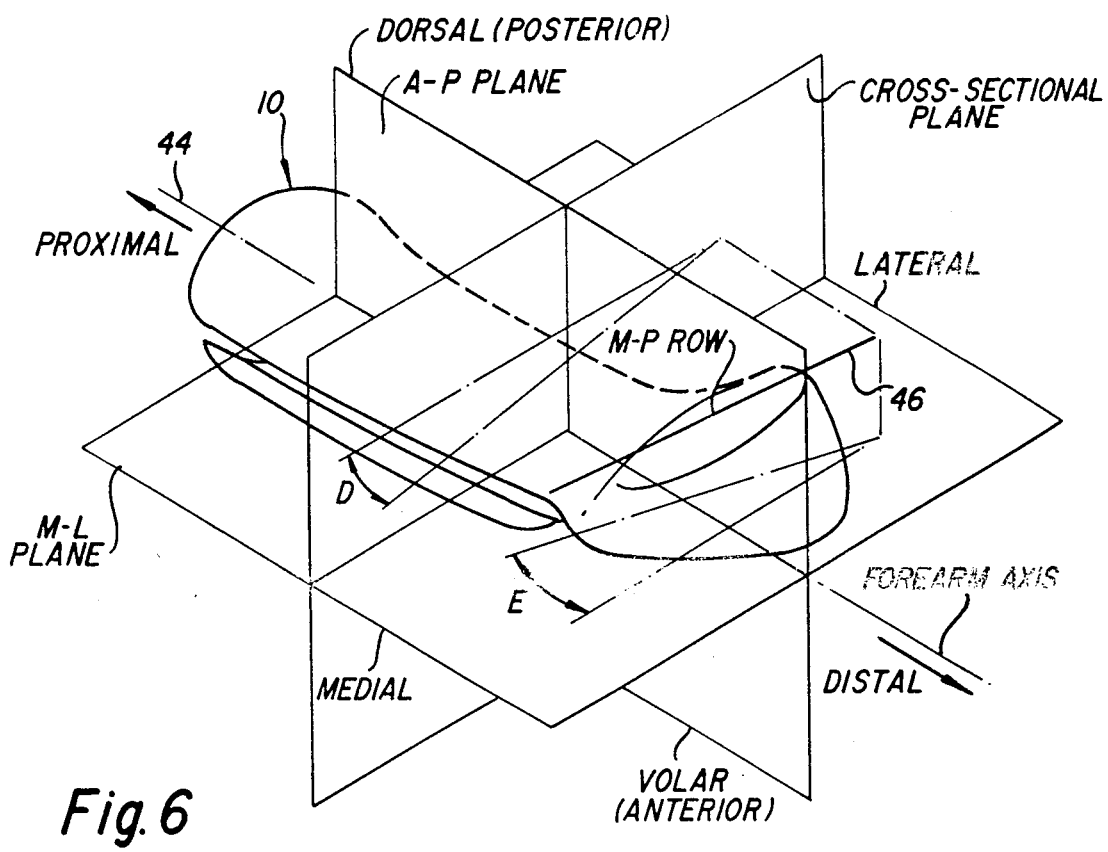
FIG. 6 is a schematic perspective view of the hand splint depicted in FIG. 1 with the various planes of an arm interposed thereon.

In order to properly position the hand of a user underneath dorsal hood 38, dorsal hood 38 is configured so that a line 46 representing the apexes of hood angle B is inclined both proximally and anteriorly as shown in FIG. 6. It should be appreciated that line 46 is parallel to the metacarpal-phalangeal joints of the user. When dorsal hood 38 is viewed perpendicular to metacarpal hood portion 40 as depicted in FIG. 3, the angle C between line 46 and line 48 which represents the axis of the hand in the plane of metacarpal hood portion 40 is approximately 60°. It should also be appreciated that this angle is not the same as the projected angle of line 46 in the cross-sectional plane depicted by angle D in FIG. 6 or the projected angle E of line 46 in the M-L plane as shown in FIG. 6. Thus, projected angles D and E are instead approximately 29° and 8°, respectively. It should also be appreciated that these angle measurements which are typically used as references by those of ordinary skill in the art are only rough approximations as the hand is curved, and that in the present invention the surfaces are actually curved as well to conform to the configuration of the hand of the user.

Also depicted in FIG. 1 is the projection of axis 50 of the metacarpals in the M-L plane. As shown, metacarpal axis 50 forms an angle F of approximately 10° with forearm axis 44.

Figure 2:
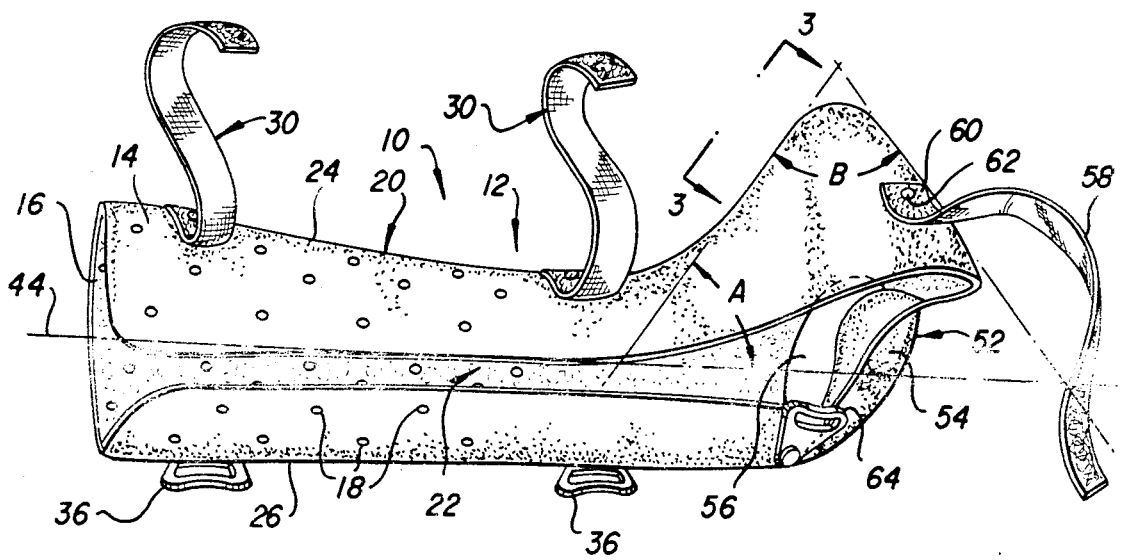
FIG. 2 is a little finger (medial) side view of the hand splint depicted in FIG. 1.
Figure 4:
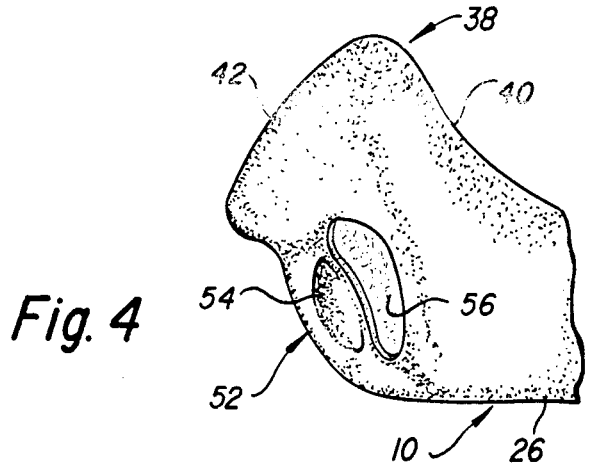
FIG. 4 is a partial thumb side (lateral) view of the hand splint depicted in FIG. 1.
Figure 5:
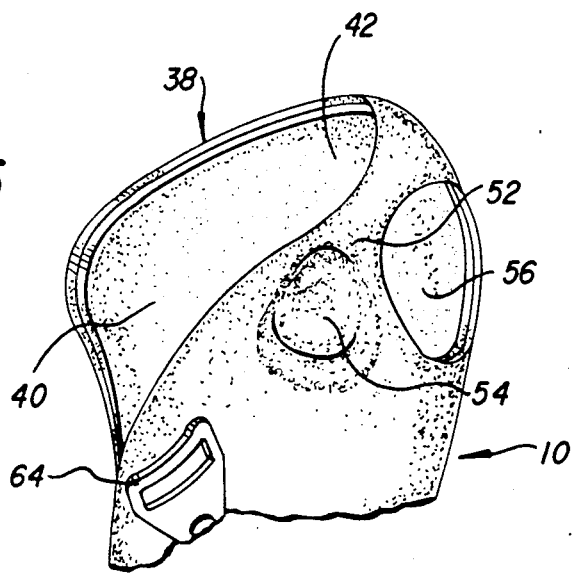
FIG. 5 is a partial anterior (volar) view of the hand splint depicted in FIG. 1.

Extending from volar shell portion 26 is a palm arch support 52. Palm arch support 52 extends adjacent metacarpal hood portion 40 in order to maintain the hand of the user in dorsal hood 38. As shown best in FIGS. 2 and 5, palm arch support 52 includes a cup shape 54 which is designed to rest against the palm of the user. Located between palm arch support 52 and dorsal hood 38 is a thumb opening 56 for the thumb of the user. In order to keep the hand of the user in position between dorsal hood 38 and palm arch support 52, a velcro strap 58 is used which is similar to velcro straps 30. Velcro strap 58 is attached at hook portion 60 to phalanx hood portion 42 by a rivet 62. Suitably attached to sleeve 12 is a ring 64 through which velcro strap 58 is looped in order to bring dorsal hood 38 and palm arch support 52 together and then to hold them in a fixed relationship.

In use, hand splint 10 functions in the following manner. Initially, straps 30 and 58 are withdrawn or substantially loosened from respective rings 36 and 64. Thus, because sleeve 12 is made from a semi-rigid material, dorsal shell portion 24 can be pulled apart from volar shell portion 26 in order to allow the insertion of a patient's hand, wrist, and distal forearm in sleeve 12. Thereafter, straps 30 are fed through respective rings 36 if needed and tensioned in order to provide some soft tissue compression in the distal forearm to aid in maintaining suspension and comfort. After proper tensioning, fibrous portion 32 of each strap 30 is attached to a respective hook portion 34 to maintain a tension in strap 30. In addition strap 58 is fed through ring 64 in order to maintain the hand of the user in position against palm arch support 52, metacarpal hood portion 40, and phalanx hood portion 42. Strap 58 is then attached to hood portion 60 to hold the hand in place.

Once hand splint 10 is attached to the hand, wrist, and distal forearm of the user, it should be appreciated that the thumb of the user extends through thumb opening 56 and provides clearance for the basar joint of the thumb so that the thumb is completely free to move at all joints. In addition, phalanx hood portion 42 covers the proximal phalanges without limiting motion of PIP and DIP joints of the fingers. It should be appreciated that hand splint 10 also initially holds the wrist in a comfortable but maximum angle of dorsiflexion of the wrist of about (or slightly less than) 75° while at the same time maintaining a maximum, comfortable dorsiflexion of slightly less than 90° of flexion of the metacarpal-phalangeal joints. After hand splint 10 is worn for a long period of time, some play will develop and the dorsiflexion angle of the wrist will be reduced. However, this angle should not be less than about 45°, and hand splint 10 is designed to maintain this minimum wrist dorsiflexion by the selection of dorsiflexion angle A between 60° to 80°. Forearm axis 44 also forms approximately a 10° angle of radial deviation to the projection of the axis of the metacarpals in the M-L plane.

With use of hand splint 10, it is possible for the user to temporarily remove hand splint 10 if desired. Furthermore, adjustments for comfort and reduced swelling are further possible as necessary or desired.

It is anticipated that hand splint 10 of the present invention will have widespread application. In addition to the treatment of wrist fractures, it is also anticipated that the hand splint of the present invention can be used to treat metacarpal fractures and certain fractures of the proximal phalanx which can be reduced by the maneuver of the metacarpal-phalanx joint flexion. It should also be appreciated that dorsal hood 38 aids in the correction dorsal edema of the hand and fingers. While hand splint 10 does not have specific uses in the management of flexor tendon injuries, by wrist flexion instead of wrist extension, it can be used to manage flexor tendon injuries.

While the present invention has been described with respect to an exemplary embodiment thereof, it will be understood by those of ordinary skill in the art that various changes and modifications can be effected within the scope and spirit of the invention.

I claim:

1. A hand splint for immobilizing a hand, wrist, and distal forearm of a user, comprising:
   a sleeve in which the hand, wrist and distal forearm are received, said sleeve being made of a semi-rigid material and including
   (a) an elongated shell adapted to extend over the wrist and distal forearm, said shell having a substantially C-shape in lateral cross section with an opening of the C-shape being adapted to be located at an M-L plane of the forearm, said shell including a dorsal shell portion and volar shell portion,
   (b) a dorsal hood extending from said dorsal shell portion, said dorsal hood including a metacarpal hood portion which is adapted to cover the dorsum of the hand and a phalanx hood portion which is adapted to cover the proximal phalanges and which terminates thereat; said metacarpel hood portion adapted to form a dorsiflexion angle of between 60° to 80° with the axis of the forearm so that a comfortable maximal dorsiflexion of the wrist is achieved; and said metacarpal hood portion forming a hood angle of between 75° to 90° with said phalanx hood portion,
   (c) a palm arch support extending from said volar shell portion, said palm arch support extending adjacent said metacarpal hood portion in order to maintain the hand in said dorsal hood with the wrist in dorsiflexion by abutment with said metacarpal hood portion and the metacarpal-phalangeal joints at an angle of greater than about 90° to 105° by abutment of the proximal phalanges with said phalanx hood portion, and
   (d) a thumb opening between said dorsal hood and said palm arch support defined by a border of said sleeve, said border being adapted to be recessed from the thumb such that the thumb of the user extends through the thumb opening and all joints of the thumb are free to move; and
   a holding means for holding said sleeve in radial abutment with the hand, wrist and distal forearm of the user.

2. A hand splint as claimed in claim 1 wherein the hood angle is slightly less than 90°.

3. A hand splint as claimed in claim 2 wherein the dorsiflexion angle is about 75°.

4. A hand splint as claimed in claim 3 wherein a line formed by the apexes of the hood angle is adapted to form an angle of about 60° with respect to the longitudinal axis of the hand projected on the metacarpal hood portion.

5. A hand splint as claimed in claim 1 wherein a line formed by the apexes of the hood angle projected onto the M-L plane forms an angle of about 80° with the forearm axis.

6. A hand splint as claimed in claim 1 wherein said holding means is at least two straps and associated securing means for securing said straps in tension across the opening of said C-shaped shell to radially compress the distal forearm, and a strap and associated securing means for securing said last-mentioned strap in tension between said palm arch support and said dorsal hood to maintain the hand in said dorsal hood.

7. A hand splint as claimed in claim 1 wherein said sleeve is covered on an inside portion thereof with a resilient material, and a plurality of apertures are provided through said sleeve and said resilient material.

8. A hand splint as claimed in claim 1 wherein the opening of said C-shaped shell is adapted to be on the little finger side of the hand.

9. A hand splint for immobilizing a hand, wrist, and distal forearm of a user, comprising:
   a sleeve in which the hand, wrist and distal forearm are received, said sleeve being made of a semi-rigid material and including
   (a) an elongate shell adapted to extend over the wrist and distal forearm, said shell having a substantially C-shape in lateral cross section with an opening of the C-shape being adapted to be located at an M-L plane of the forearm on the little finger side of the hand, said shell including a dorsal shell portion and volar shell portion,
   (b) a dorsal hood extending from said dorsal shell portion, said dorsal hood (i) including a metacarpal hood portion which is adapted to cover the dorsum of the hand and a phalanx hood portion which is adapted to cover the proximal phalanges and which terminates thereat, (ii) being adapted to form a dorsiflexion angle of about 75° with the axis of the forearm so that a comfortable maximal dorsiflexion of the wrist is achieved, (iii) forming a hood angle of slightly less than 90° with said phalanx hood portion, and (iv) being adapted to have the apexes of said hood angle forming an angle of about 60° with respect to the longitudinal axis of the hand projected on said metacarpal hood portion;

(c) a palm arch support extending from said volar shell portion, said palm arch support extending adjacent said metacarpal hood portion in order to maintain the hand in said dorsal hood with the wrist in dorsiflexion by abutment with said metacarpal hood portion and the metacarpal-phalangeal joints at an angle of greater than about 90° by abutment of the proximal phalanges with said phalanx hood portion, and (d) a thumb opening between said dorsal hood and said palm arch support defined by a border of said sleeve, said border being adapted to be recessed from the thumb such that the thumb of the user extends from the thumb opening and all joints of the thumb are free to move; and a holding means for holding said sleeve in radial abutment with the hand, wrist and distal forearm of the user.

* * * * *